United States Patent [19]
Sakai et al.

[11] Patent Number: 5,644,066
[45] Date of Patent: Jul. 1, 1997

[54] METHODS FOR INTRODUCING A FERTILITY RESTORER GENE AND FOR PRODUCING F₁ HYBRID OF BRASSICA PLANTS THEREBY

[75] Inventors: Takako Sakai, Machida; Hongjun Liu, Yokohama; Hiroyuki Kurihara; Jun Imamura, both of Machida, all of Japan

[73] Assignee: Mitsubishi Chemical Corporation, Tokyo, Japan

[21] Appl. No.: 136,023

[22] Filed: Oct. 14, 1993

[30] Foreign Application Priority Data

Oct. 14, 1992 [JP] Japan .................. 4-276069
Oct. 14, 1992 [JP] Japan .................. 4-276070
Oct. 15, 1992 [JP] Japan .................. 4-303127

[51] Int. Cl.⁶ .............. A01H 5/00; A01H 1/02; C12N 5/14; C12N 15/02
[52] U.S. Cl. .............. 800/220; 800/200; 800/205; 800/250; 800/255; 800/DIG. 15; 800/DIG. 17; 435/172.2; 47/58
[58] Field of Search ............ 800/200, 205, 800/220, 250, 255, DIG. 17, DIG. 15; 435/240.1, 240.4, 240.47, 240.49, 240.5, 172.2, 240.46; 47/58.03, 58.04, 58.05, 58

[56] References Cited

FOREIGN PATENT DOCUMENTS

| 0214601 | 3/1987 | European Pat. Off. |
| 8403606 | 9/1984 | WIPO |
| 84-03606 | 9/1984 | WIPO |
| 87-01726 | 3/1987 | WIPO |
| 92-05251 | 4/1992 | WIPO |
| 92-132121/16 | 4/1992 | WIPO |
| 92/05251 | 4/1992 | WIPO |

OTHER PUBLICATIONS

Genome, R. Pellan–Delourme et al., "Cytoplasmic Male Sterility in Rapessed (*Brassica napus* L.): Female Fertility of Restored Rapeseed with Ogura and Cybrids Cytoplasms", vol. 30, 1988, pp. 234–238.

Mol. Gen. Genet., G. Pelletier et al., "Intergeneric Cytoplasmic Hybridization in Cruciferae by Protoplast Fusion", (1983) 191:244–250.

Paulmann et al., Plant Breeding, "Effective Transfer of Cytoplasmic Male Sterility from Radish (*Raphanus sativus* L.) to Rape (*Brassica napus* L.)¹)", vol. 100, pp. 299–309 (1988).

Bajaj, Biotechnology in Agriculture and Forestry, vol. 10, "Legumes and Oilseed Crops I", Ch. IV. 3, pp. 418–433 (1990).

Poehlman, Breeding field Crops, Ch. 7, "Fertility Regulating Mechanisms and Their Manipulation", pp. 129–147 (1986).

Pelletier et al., Molecular and General Genetics, "Intergeneric Cytoplasmic Hybridization in Cruciferae by Protoplast Fusion", vol. 191, pp. 244–250 (1983).

Harbred et al. 1969. Euphytica. 18;425–429.

Heyn. 1978. Proceedings 5th International Rapeseed Conference vol. 1:82–83.

Dolstra. 1982. Synthesis and fertility of x Brassicoraphanus and Ways of Transferring Raphanus characters to Brassica. pp. 1–90. Agricultural Research Reports. Wageningen.

*Primary Examiner*—David T. Fox
*Assistant Examiner*—Melissa L. Kimball
*Attorney, Agent, or Firm*—Wenderoth, Lind & Ponack

[57] ABSTRACT

A method is provided for introducing a fertility restorer gene of a Raphanus plant into a Brassica plant by means of cell fusion or intergeneric cross and a Brassica plant produced thereby. Also provided is a method for producing an F₁ hybrid of a rapeseed plant utilizing Kosena-radish-derived CMS gene and a fertility restorer gene derived from any of the radish plants and an F₁ hybrid of a rapeseed plant produced thereby.

20 Claims, 3 Drawing Sheets

TRANSFER OF RESTORER GENE FROM R. SATIVUS TO B. NAPUS THROUGH INTERGENERIC CROSS

METHODS FOR INTRODUCING A FERTILITY RESTORER GENE AND FOR PRODUCING $F_1$ HYBRID OF BRASSICA PLANTS THEREBY

BACKGROUND OF THE INVENTION

1. Field of the Invention

The present invention relates to a method for introducing a fertility restorer gene (Rf gene) of a Raphanus plant into a Brassica plant by means of cell fusion or intergeneric cross and a Brassica plant produced thereby. It also relates to a method for producing a commercial first filial generation ($F_1$) hybrid of a rapeseed plant utilizing a Kosena-radish-derived cytoplasmic male sterility gene and a fertility restorer gene derived from any of the radish plants and an $F_1$ hybrid plant of a rapeseed plant produced thereby.

2. Description of Related Art

Breeding of rapeseed plants has been centered on open-pollinated seeds by taking advantage of high self-compatibility affinity of said plants. Breeding of an $F_1$ hybrid showing a remarkable heterosis has been practically employed in numerous plants. This method has been applied to the breeding of rapeseed plants too. An $F_1$ plant often shows advantages due to the expression of heterosis. Thus, it has excellent agricultural characteristics such as yield and disease resistance and the breed grown therefrom has relatively uniform characteristics. Further, benefits of a breeder can be protected because of the segregation of generic characteristics in the following generation.

Breeding of $F_1$ hybrid of rapeseed plants has been attempted by utilizing self-incompatibility or cytoplasmic male sterility (hereinafter, referred to as CMS). The method involving CMS is considered to be more hopeful in terms of efficiency of seed production and facility of maintenance of mating parents.

The only CMS used in the commercial production of $F_1$ hybrid of rapeseed plants was that derived from a rapeseed plant Polima. The Polima-derived CMS, however, has problems such as instability of male sterility under high temperature. Thus, the pollen fertility can be restored depending on temperature of the flowering period. As a result, the $F_1$ hybrid lack in homogeneities of the typical $F_1$ hybrid. In some cases where incompatibility between certain nuclear background and Polima CMS has occurred, the resulting $F_1$ hybrid plants may be small in size and do not express the heterosis which is one of the most important characteristics of the $F_1$ hybrids.

The present inventors have previously disclosed a method for introducing cytoplasmic gene of radish directly from its protoplast to a protoplast of Brassica plant such as rapeseed, which method comprises fusing radish-derived protoplast previously irradiated with X-ray with Brassica-derived protoplast previously treated with iodinated compound (Japanese Patent Publication (KOKAI) No. 218530/1989). Also disclosed has been a method for introducing a cytoplasmic gene of radish directly from its cytoplast to a protoplast of Brassica plant such as rapeseed, which method comprises fusing radish-derived cytoplast with Brassica-derived protoplast previously treated with iodinated compound (Japanese Patent Publication (KOKAI) No. 303426/1990). To produce an $F_1$ hybrid seed, it is necessary that either of the parents has a fertility restorer gene (Rf gene). In our previous methods described above, a radish-derived CMS gene can be introduced into rapeseed though, it was also required to introduce radish-derived Rf gene because the rapeseed lacks an Rf gene corresponding to said CMS gene. Introduction of a radish Rf gene into a rapeseed plant can be effected by any of the known methods such as intergeneric cross method. The intergeneric cross method, however, involves various generic or physiological problems such as hybridization incompatibility, lethality of resultant hybrid and the like, and therefore said method is hardly applicable to obtain desired hybrids. Although introduction of a radish Rf gene into a rapeseed plant by means of intergeneric cross has been reported in case of Tokumasu's CMS (W. Paulmann & G. Robbelen, Plant Breeding, 100, 299–309 (1988)) and Ogura's CMS (R. Pellandelourme et al., 7th International Rapeseed Congress (1987)), they have not been employed practically. As to the introduction of radish gene into rapeseed plant by means of cell fusion, there have been no reports.

SUMMARY OF THE INVENTION

The present inventors have found that CMS and a corresponding Rf gene of a Raphanus plant such as radish are useful to obtain a commercial $F_1$ hybrid of a Brassica plant such as rapeseed, said breed expressing stably and with high heterosis. Thus, an Rf gene of a Raphanus plant can be efficiently introduced into a Brassica plant by means of intergeneric cross in combination with a modified ovary culture procedure, or by means of cell fusion.

Further, the present inventors have conducted research with the purpose of breeding excellent $F_1$ hybrid which avoid the above-mentioned problems accompanying the method involving cytoplasm of Polima. The inventors have established the present invention by using CMS derived from Kosena-radish (*Raphanus sativus*, cv. Kosena) together with an Rf gene derived from any of radish plants, said Rf gene being capable of restoring the fertility of CMS of the former plant.

Thus, the present invention provides a method for introducing an Rf gene corresponding to CMS of Raphanus into a plant of Brassica characterized in that cell fusion or intergeneric cross is conducted and a Brassica plant to which an Rf gene of Raphanus plant has been introduced. It also provides a method for producing an $F_1$ hybrid of a rapeseed plant characterized in that hybridization is conducted using as a pollen recipient line a rapeseed CMS line to which CMS of Kosena-radish has been introduced and as a pollen donor line a rapeseed fertility restorer line to which a radish-derived Rf gene which can restore the pollen fertility resulting from Kosena radish-derived CMS has been introduced, and an $F_1$ hybrid of rapeseed plant produced thereby.

DETAILED DESCRIPTION OF THE INVENTION

Figure 1:
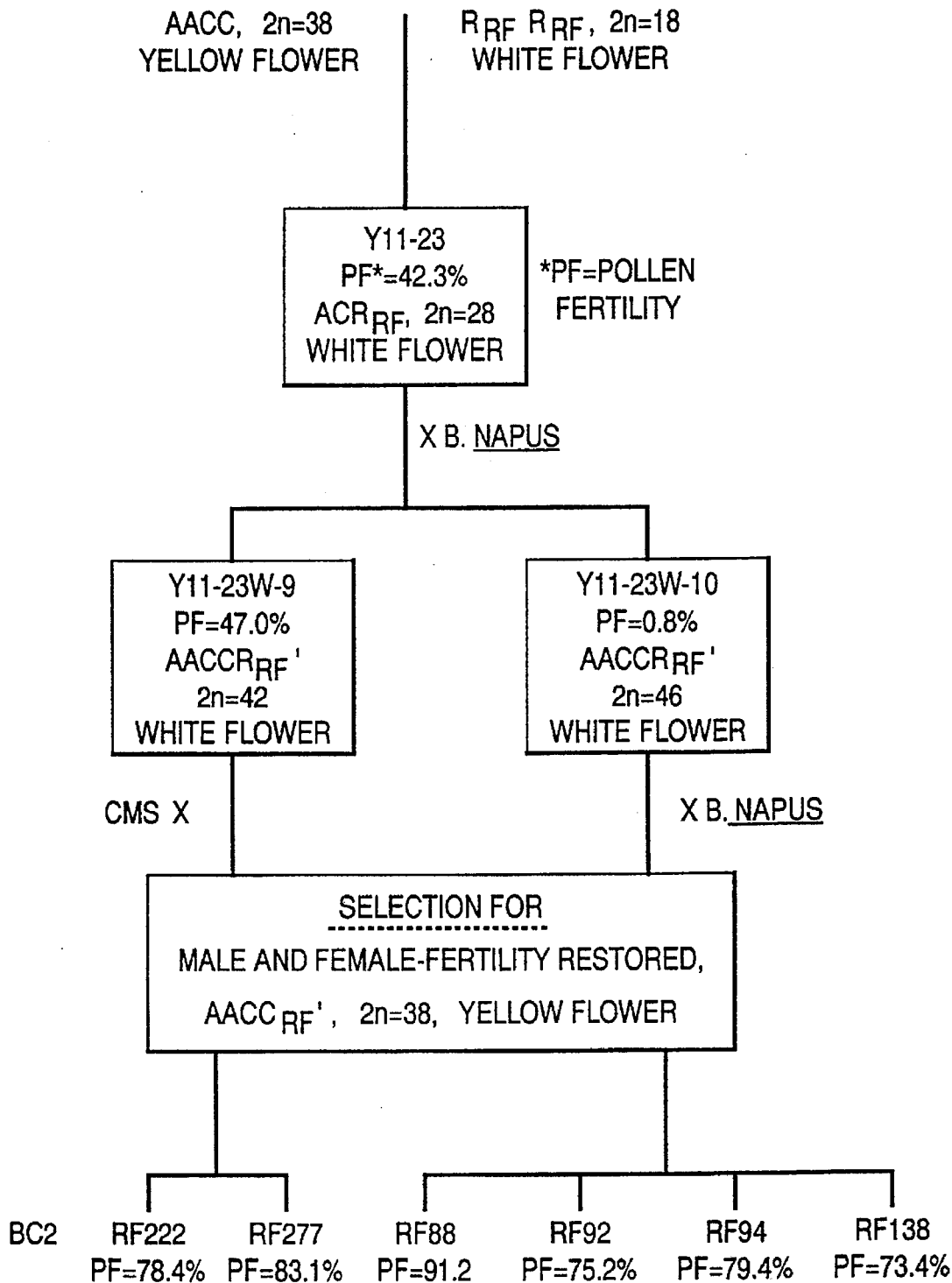
FIG. 1 is a flow diagram showing the breeding of rapeseed restorer lines which comprises the preparation of $F_1$ hybrid by intergeneric cross between CMS rapeseed and Chinese radish cultivar Yuanhong followed by serial backcross of said $F_1$ hybrid with a rapeseed.

Examples of Brassica plant usable in the present method include any plants to which CMS of a Raphanus plant has been introduced or elite lines having normal cytoplasm. A rapeseed (*Brassica napus*) is preferable and, specifically, a rapeseed Westar (*Brassica napus* cv. Westar) to which CMS of Kosena-radish has been introduced or elite lines thereof are more preferred.

Examples of a Raphanus plant usable in the present method include any plant lines or cultivars provided that the plant contains the Rf gene of a Raphanus plant. In the present invention, radish (*Raphanus sativus*) is preferably employed, and Japanese Kosena-radish (*R. sativus*, cv. Kosena) and Chinese radish cultivars Yuanhong (*R. sativus*, cv. Yuanhong) and Xinlimei (*R. sativus*, cv. Xinlimei) are more preferred.

According to the present invention, a fertility restorer gene can be introduced into a Brassica plant by means of cell fusion or intergeneric cross procedure.

In case of cell fusion, protoplasts of Brassica plant and Raphanus plant mentioned above are first prepared.

The preparation of protoplasts can be carried out according to any of the standard procedures, for example, by mincing hypocotyls or leaves of a plantlet into small pieces and immersing the pieces in an iso-osmotic solution containing cell wall digesting enzyme such as cellulase or pectinase at 25° to 30° C. for 5 to 20 hours.

Fusion of purified protoplasts can be effected by, for example, polyethylene glycol (PEG) method. Examples of fusion methods include symmetric fusion in which both protoplasts are fused to each other directly and asymmetric fusion in which one of the protoplasts contains inactivated nucleus so as to introduce only specific genes. For purposes of the present invention, the latter method is preferable. Thus, protoplasts derived from a Raphanus plant are irradiated with X-ray (10 to 300 KR), γ-ray, ultraviolet light or the like to impair the nuclear DNA to some extent. On the other hand, protoplasts of a Brassica plant are treated with 2 to 40 mM iodinated compound (iodoacetoamide, iodoacetic acid and the like) at room temperature for 5 to 30 minutes to inactivate the cytoplasm.

Thus treated protoplasts are fused, for example, by PEG method as will hereinafter be explained in detail.

Fusion was carried out in W5 solution containing 6.7 to 50% PEG (Plant Cell Report, 3, 196–198 (1984), Plant Science, 43, 155–162 (1986)). Protoplasts are added to the solution in a ratio from 3:1 to 1:3 (Brassica:Raphanus) in such amounts that the total cell density is 1 to $4\times10^6$ cells/ml, and fusion is conducted at room temperature. Examples of PEG usable include those having molecular weight of 1500 available from Boehringer Mannheim, Inc. or the like.

After the fusion of protoplasts, PEG is removed and a suitable protoplast medium, such as, for example, KM liquid medium (Planta, 126, 105 to 110, (1975)) which contains 0.05 to 0.5 mg/l 2,4-di-chlorophenoxyacetic acid (2,4-D), 0.02 to 0.5 mg/l naphthalene acetic acid (NAA), 0.1 to 2.0 mg/l benzylaminopurine (BAP) and 0.4M glucose is added and incubated for about one week. To the mixture is added an equal volume of KM medium containing 0.1M sucrose, 0.2 to 3.0 mg/l 2,4-D, 0.02 to 0.5 mg/l NAA and 0.1 to 2.0 mg/l BAP is added. When the incubation is continued for about 3 weeks, numerous colonies having diameters from 0.5 to 1 mm are formed. At this point of the time, the colonies are transferred to a callus proliferation medium, such as, for example, MS solid medium containing 0.5 to 2 mg/l 2,4-D, 0.1 to 0.5 mg/l BAP, 1 to 5% sorbitol, 1 to 5% sucrose, 0.5 to 2 g/l casein hydrolysate (CH) and 0.5 to 1% agar (Murashige & Skoog, 1962), and then incubated for 2 to 3 weeks under dim light to yield green callus.

The resulting callus is transferred immediately to re-differentiation medium, such as MS solid medium containing 0.01 to 0.1 mg/l NAA, 0.5 to 2 mg/l BAP, 1 to 5% sorbitol, 0.5 to 2% sucrose, 0.05 to 0.5 g/l CH and 0.5 to 1% agar to regenerate shoots. In the present invention, the regenerated shoot is further transferred to a suitable medium for the development of roots, such as, for example, MS solid medium containing 0.05 to 0.2 mg/l NAA, 0.01 to 0.05 mg/l BAP, 1 to 5% sucrose and 0.2% Gelite (Kelco, Division of Merck & Co., Inc.) to obtain a normal plantlet. Finally, the plantlet is transplanted to Vermiculite (Showa Vermiculite) supplemented with about 1000-fold diluted Hyponex (Murakami Bussan), covered with, for example, air-permeable Miliwrap (Milipore) instead of tube cap, and grown to obtain a Brassica somatic hybrid plant to which an Rf gene of Raphanus is introduced. From the resultant hybrid plants are screened individual breed to which the Rf gene has been introduced on the basis of pollen fertility, number of chromosomes or the like. A morphologically normal and cytologically stable Brassica plant having an Rf gene of Raphanus plant can be obtained through a serial backcross with a Brassica plant, if desired.

The introduction of a fertility restorer gene by intergeneric cross procedure will be explained below.

In the present method, intergeneric cross is first conducted between a Brassica plant and a Raphanus plant having a fertility restorer gene corresponding to CMS. Thus, Brassica flowers (in case of cultivar, anthers should be emasculated previously) are subjected to pollination with pollens of a Raphanus plant.

Subsequently, 3- to 10-day ovaries are harvested, sterilized and placed on a solid medium, such as, for example, Nitsch & Nitsch (1967) agar plate. The medium preferably contains 0.1 to 1 g/l casein hydrolysate (CH) and 1 to 10% coconut milk (CM). The concentration of sucrose may be 3 to 8%. The incubation can preferably be performed in a chamber thermostated at $25°\pm1°$ C., under fluorescent lighting at 500 to 1000 lux for a daily lighting period from 12 to 14 hours.

After 2- to 4-week-incubation, a grown hybrid embryo is isolated from a pod and germination is effected by planting the embryo in MS medium (Murashige & Skoog, 1962) or B5 medium (Gamborg et al., 1968), said medium being hormone-free or containing 0.05 to 0.2 mg/l benzylaminopurine (BAP). The embryos which developed leaves are transplanted to a medium for inducing the development of roots (MS medium containing 0.05 to 0.1 mg/l NAA and 0.01 to 0.05 mg/l BAP) to obtain a normal plantlet into which the Rf gene of Raphanus has been introduced. As to embryos failed to develop leaves, re-differentiation can be effected by subjecting hypocotyles to comminution and placing in MS solid medium supplemented with 0.1 to 2 mg/l NAA or indoleacetic acid (IAA), 0.1 to 2 mg/l BAP and 0.1 to 2 g/l CH. The resulting shoots, when subjected to the induction of the development of roots in a manner similar to that used for normally germinated, grow to a normal plant into which the Rf gene of Raphanus has been introduced.

For acclimatization of the plant, Vermiculite bed (Showa Vermiculite) supplemented with, for example, diluted Hyponex (Murakami Bussan) as a nutrient may be employed. In the present invention, efficient acclimatization of the hybrid plant can be achieved by the use of Vermiculite and air-permeable Miliwrap (Milipore).

When the resultant hybrid plant is used as a pollen parent or mother for serial backcross with Brassica napus, *Brassica campestris* or the like, a morphologically normal and cytological stable Brassica plant having the Rf gene of Raphanus can be obtained.

A method for producing an $F_1$ hybrid of rapeseed plants will be explained in detail below.

The $F_1$ hybrid of rapeseed of the present invention can be produced by breeding a rapeseed pollen recipient line with a rapeseed pollen-donor line. Each line can be produced as follows.

The rapeseed pollen recipient line having CMS of Kosena-radish can be produced by fusing Kosena-radish-derived cytoplast or irradiated (X-ray, γ-ray, UV, etc.) protoplast with a rapeseed (i.e., *Brassica napus*)-derived protoplast treated with an iodinated compound (iodoacetoamide, iodoacetic acid, etc.) and then incubating the fused cells until colonies are formed. From colonies, shoots are re-generated to grow the desired rapeseed pollen recipient line (Japanese Patent Publication (KOKAI) No. 218530/1989; Japanese Patent Publication (KOKAI) No. 303426/1990 and the like). CMS of Kosena-radish has excellent features and is highly stable in male sterility which is not affected by any factors such as temperature and is never restored. This pollen recipient line may further be hybridized with an optional cultivars or lines of rapeseed if desired. Examples of usable rapeseed plants include spring-type rapeseed cultivar Westar (*B. napus* cv. Westar) and the like.

The pollen-donor line having the Rf gene corresponding to CMS of Kosena-radish can be produced by hybridization (mating) or cell fusion as described above using CMS line mentioned above, or optional cultivar or line of rapeseed and a radish plant having an Rf gene capable of restoring the pollen fertility against Kosena-radish-derived CMS. This pollen-donor line may further be hybridized with optional rapeseed cultivar or line. The genome constituent of a hybrid plant obtained from a rapeseed (*Brassica napus*; genome constituent, AACC) and a radish (*Raphanus sativus*; genome constituent, RR) is ACR. Although hybridization can be carried out by the backcross of a rapeseed (*B. napus*), there are other methods applicable to the present invention. For example, $F_1$ plant (ACR genome) of rapeseed and radish is treated with colchicine to double the chromosome to obtain a hybrid plant having the genome of AACCRR, with which a rapeseed (*B. campestris*; AA genome) is then hybridized to induce recombination of C genome with R genome, whereby yielding a plant having the genome of AAC'R'. Alternatively, a hybrid plant having the genome of AAC-CRR can be obtained by the cell fusion of the rapeseed and the radish. Examples of radish usable are Japanese Kosena-radish, Chinese Yuanhong (*R. sativus*, cv. Yuanhong) and Xinlimei (*R. sativus*, cv. Xinlimei), and examples of rapeseed usable are spring-type rapeseed cultivar "Westar" and the like.

According to the present invention, despite the difference in biological genus, an Rf gene of a Raphanus plant can be introduced into a Brassica plant within a short period by means of cell fusion, especially, asymmetric cell fusion method, or by means of intergeneric cross method. Thus, as the result of the present invention, it becomes possible to put the $F_1$ hybrid breeding of Brassica utilizing CMS derived from Raphanus to practical use.

Furthermore, as the present invention utilizes the Kosena-radish-derived CMS which is superior to conventional CMSs, more excellent breeding of $F_1$ hybrid of rapeseed plants can be attained.

The following Examples are provided to further illustrate the present invention and are not to be construed as limiting thereof.

EXAMPLE 1

Introduction of Rf Gene by Cell Fusion (1) Preparation of protoplast from radish Leaves were collected from a sterile seedling of Kosena-radish having an Rf gene, and comminuted in an enzyme solution and allowed to stand at 25° C. in a dim place overnight. The enzyme solution was NN67 medium (Nitsch & Nitsch, 1967) containing 0.35M sucrose, 0.5 ml/l 2,4-D, 0.5 mg/l NAA and 1 mg/l BAP supplemented with 0.5% cellulase R-10, 2% cellulase RS, 0.05% Macerozyme R10 and 0.02% pectoriase Y-23.

After enzymatic treatment, the enzyme solution was filtered to remove non-digested substances, and then the filtrate was centrifuged at 800 rpm for 10 minutes to collect precipitations. The precipitations were placed gently onto 0.6M sucrose solution, which was then centrifuged for 10 minutes at 800 rpm to collect the band of protoplasts.

(2) X-ray irradiation

The protoplasts purified in (1) above was adjusted to $10^6$ cells/ml, and then irradiated with X-ray (60K Roentgen in total).

(3) Preparation of protoplast from rapeseed

Seeds of a CMS rapeseed (*Brassica napus*, cv. Westar) were allowed to germinate under a sterile condition. On the 4th to 6th day, the hypocotyles were taken, comminuted in the enzyme solution and allowed to stand at 25° C. in a dim place overnight. The enzyme solution was an inorganic solution consisting of NN67 medium (Nitsch & Nitsch, 1967) containing 0.4M sucrose and 0.1% MES (Dojin Kagaku) supplemented with 2% cellulase RS and 0.01% pectolyase Y-23. After enzymatic treatment, the enzyme solution was filtered to remove non-digested substances, and then the filtrate was centrifuged at 800 rpm for 10 minutes to collect upper layer protoplast fraction.

(4) Iodoacetoamide treatment

The protoplasts recovered in (3) above were suspended in W5 solution at concentration of $2 \times 10^5$ cells/mi. To this suspension 100 mM iodoacetoamide solution was added to make the final concentration of 10 mM. The suspension was allowed to stand for 10 minutes at room temperature and centrifuged at 800 rpm for 5 minutes to collect the protoplasts, which were washed three times with W5.

(5) Cell fusion

The protoplasts of Kosena-radish which had been irradiated with X-ray and the protoplasts of rapeseed which had been treated with iodoacetoamide were admixed in the ratio of 2:1 to obtain a suspension of final concentration of $2 \times 10^6$ cells/mi. Three or four drops of the suspension, each amounting to 100 μl, were added dropwise onto a 6 cm petri dish. After allowing to stand for 5 minutes to ensure sedimentation of cells contained in the drops, 100 μl of W5 containing 40% PEG was added carefully to each drop, and the dish was allowed to stand for another 5 minutes. After removal of 40% PEG with suction, cells were treated similarly with W5 containing 13% PEG and W5 containing 6.7% PEG.

(6) Incubation of fused cells

PEG fluid was sucked off completely. To each dish was added 3 ml of KM liquid medium containing 0.4M glucose, 1 mg/l 2,4-D, 0.1 mg/l NAA and 0.4 mg/l BAP and then incubated at 25°±1° C. under a light of low intensity. After 1 week, KM solution similar to that described above except that it contains 0.1M sucrose instead of 0.4M glucose was added in an equal volume. After further incubation for 2 to 3 weeks, numerous colonies were formed.

These colonies were transplanted to MS medium containing 1 mg/l 2,4-D, 0.25 mg/l BAP, 3% sorbitol, 2% sucrose, 1 g/l CH and 0.5% agar, and allowed to proliferation. Callus was transplanted to MS medium containing 0.02 mg/l NAA, 2 mg/l BAP, 3% sorbitol, 0.5% sucrose, 0.1 g/l CH and 0.6% agar to induce shoot regeneration.

When regenerated shoots were transplanted to MS medium containing 1 mg/l NAA, 0.01 mg/l BAP, 3% sucrose and 0.2% Gelite to induce root formation, normal plantlets were obtained.

The acclimatization of somatic hybrid plants was easily established by transplanting plantlet developing leaves and roots to Vermiculite supplemented with 1000-fold diluted Hyponex while using air-permeable Miliwrap instead of tube cap. The hybrid plants thus obtained exhibited high fertility and had chromosomes in the same number as that of rapeseed (2n=38).

When individual plant was subjected to self-pollinated, a morphologically normal and cytologically stable rapeseed having the Rf gene of radish was obtained. When this plant was further hybridized with a CMS rapeseed, sufficient amount of $F_1$ hybrid seeds, which exhibited high heterosis without female sterility, were obtained similarly as in the case where a standard rapeseed breed was hybridized as a pollen parent.

EXAMPLE 2

Introduction of Rf Gene by Intergeneric Cross

A rapeseed having CMS gene of Kosena-radish (*B. napus*, CMS line) was pollinated with Kosena-radish having corresponding Rf gene (*R. sativus*, cv. Kosena), and Chinese radishes Yuanhong (*R. sativus*, cv. Yuanhong) and Xinlimei (*R. sativus*, cv. Xinlimei). Four to seven days after the pollination, ovaries were isolated and subjected to sterilize with 0.5% sodium hypochlorite for 10 minutes. After washing 3 times with sterilized water, the ovaries were planted in plastic dishes of 10 cm in diameter, each containing 20 ml of agar medium. The medium was prepared by adding White's vitamin (1943), 300 mg/l CH, 2% CM and 5% sucrose to Nitsch & Nitsch's inorganic salts (1967) and solidified with 0.6% agarose. Incubation was conducted in a chamber thermostated at 25°±1° C. with lighting period for 14 hours a day under the fluorescent light at 1000 lux.

The development of hybrid embryos was observed after the 1 month culture, when embryos were isolated from the pods under an aseptic condition and transplanted to B5 medium containing 0.1 mg/l BAP for germination. Those exhibiting normal germination were transplanted in MS medium containing 0.1 mg/l NAA, 0.01 mg/l BAP, 3% sucrose and 0.2% Gelite (Kelco, Division of Merck & Co., Inc.) to induce the development of roots, and then allowed to grow to healthy normal plant. On the other hand, those failed to exhibit normal development of leaves were subjected to re-differentiation by comminuting extended hypocotyles into 3 to 5 mm pieces and then transferring onto MS medium containing 1 mg/l BAP, 0.25 mg/l NAA, 500 mg/l CH, 1% sucrose and 0.6% agarose. The regenerating shoots, when induced for the development of roots in a manner similar to that used in the cases of those exhibiting normal germination, grew into healthy normal plant.

The acclimatization of the plants were efficiently achieved by transplanting plantlets showing development of leaves and roots on sterilized Vermiculite supplemented with 1000-fold diluted Hyponex while using air-permeable Miliwrap instead of tube cap.

According to the procedures described above, CMS rapeseed (*Brassica napus*, CMS line; genome: AACC, 2n=38, flower color: yellow) was hybridized with each of Kosena-radish (*Raphanus sativus*, cv. Kosena; genome: $R_{Rf}R_{Rf}$, 2n=18, flower color: white), Yuanhong (*Raphanus sativus*, cv. Yuanhong; genome: $R_{Rf}R_{Rf}$, 2n=18, flower color: white) and Xinlimei (*Raphanus sativus*, cv. Xinlimei; genome: $R_{Rf}R_{Rf}$, 2n=18, flower color: white), and 944 ovaries in total were incubated. As a result, 285 hybrid $F_1$ hybrid plant bodies were obtained (mean growth rate =30.2%). Since the growth rate in intergeneric hybrids has generally been 2 to 5%, the growth rate of the $F_1$ plants of the present invention are remarkably high. For example, the $F_1$ line (Y11-23) obtained by the hybridization between CMS rapeseed and Yuanhong showed the pollen fertility of 42.3%, genome constituent of $ACR_{Rf}$, chromosome number of 2n=28 and the flower color of white.

Each of $F_1$ hybrids thus obtained was employed as the pollen parent or mother to conduct serial backcross with a rapeseed (*Brassica napus*, cv. Westar) or Campestris (*Brassica campestris*, cv. Tobin), and then screened based on the pollen fertility, female fertility as well as number of chromosomes. As a result, a morphologically normal and cytologically stable rapeseed restorer lines having the Rf gene of radish were obtained. For example, when Y11-23W-9 line (pollen fertility: 47.0%, genome: $AACCR_{Rf}$, 2n=42, flower color: white) obtained by backcross between Y11-23 line and a rapeseed was subjected to backcross with CMS rapeseed, RF222 line (pollen fertility: 78.4%, genome: $AACC_{Rf}$, 2n=38, flower color: yellow), RF277 line (pollen fertility: 83.1%, genome:/$AACC_{Rf}$, 2n=38, flower color: yellow) and the like were obtained. When Y11-23W-10 line (pollen fertility: 0.8%, genome: $AACCR_{Rf}$, 2n=46, flower color: white) obtained by backcross between Y11-23 line and a rapeseed was subjected to backcross with a rapeseed, RF88 line (pollen fertility: 91.2%, genome: $AACC_{Rf}$, 2n=38, flower color: yellow), RF92 line (pollen fertility: 75.2%, genome: $AACC_{Rf}$, 2n=38, flower color: yellow), RF94 line (pollen fertility: 79.4%, genome: $AACC_{Rf}$, 2n=38, flower color: yellow) and RF138 line (pollen fertility: 73.4%, genome: $AACC_{Rf}$, 2n=38, flower color: yellow) were obtained (see, Table 1 below).

TABLE 1

Characteristics of Rapeseed Restorer Lines to Which Radish-derived Fertility Restorer Genes were Introduced

| Restorer Gene | Flower Color | Number of Chromosomes | Pollen Fertility (%) |
| --- | --- | --- | --- |
| RF 88 | Yellow | 38 | 91.2 |
| RF 92 | Yellow | 38 | 75.2 |
| RF 94 | Yellow | 38 | 79.4 |
| RF138 | Yellow | 38 | 73.4 |
| RF222 | Yellow | 38 | 78.4 |
| RF277 | Yellow | 38 | 83.1 |

These restorer lines were maintained easily by self-pollination, and, when hybridized with CMS rapeseed, provided $F_1$ hybrid showing high heterosis.

EXAMPLE 3

Production of $F_1$ Hybrid of Rapeseed
(1) Breeding of pollen recipient line

Cell fusion was carried out in a manner analogous to that described in Japanese Patent Publication (KOKAI) No. 303426/1990 using protoplasts derived from a spring-type rapeseed cultivar Westar and cytoplasts derived from Kosena-radish having CMS. Male sterile plants were obtained from the protoplast or cytoplast fusion experiments. The male sterile plant was subjected to backcross three times with Westar to produce a pollen recipient line SW18-3. As can be seen from Table 2 below, SW18-3 lines having CMS derived from Kosena-radish did not show the restoration of pollen fertility in all cases, indicating that said lines are characteristically stable in sterility.

TABLE 2

| Condition for Growing | Number of flowers investigated | Number of flowers showing restored fertility | Fertility restoration rate (%) |
|---|---|---|---|
| Plastic plant house (15–25° C.) | 375 | 0 | 0 |
| Biotron (15° C.) | 223 | 0 | 0 |
| Biotron (23° C.) | 248 | 0 | 0 |

Figure 2A:
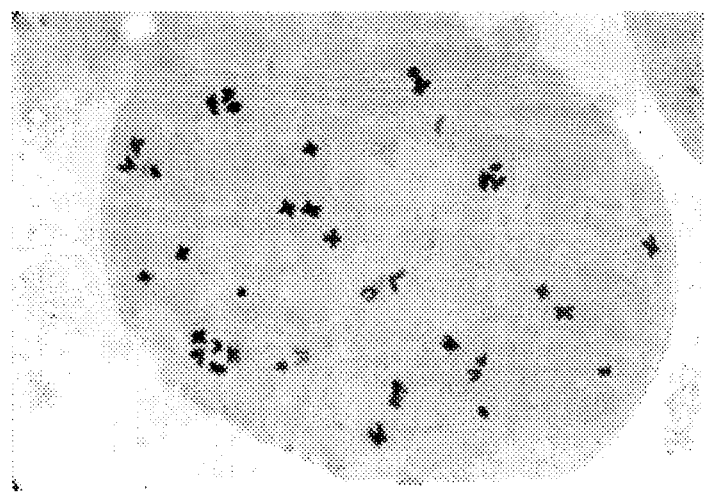
FIG. 2 shows photographs of a flower (c), pollen (b) and chromosomes (a) of the rapeseed restorer line RF88 into which fertility restorer gene of a radish was introduced.
Figure 2B:
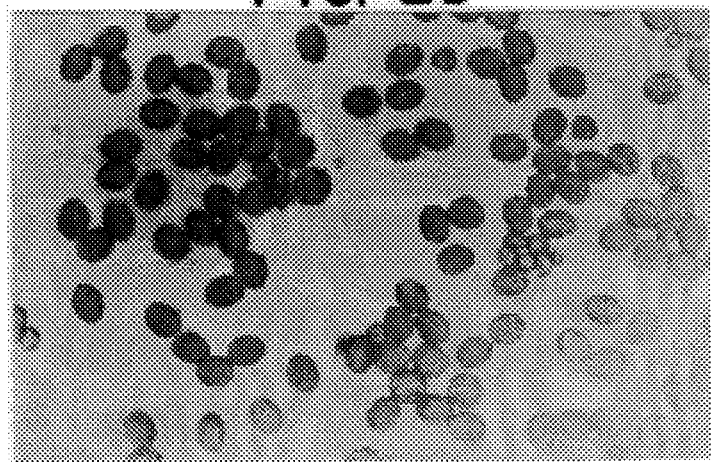
Figure 2C:
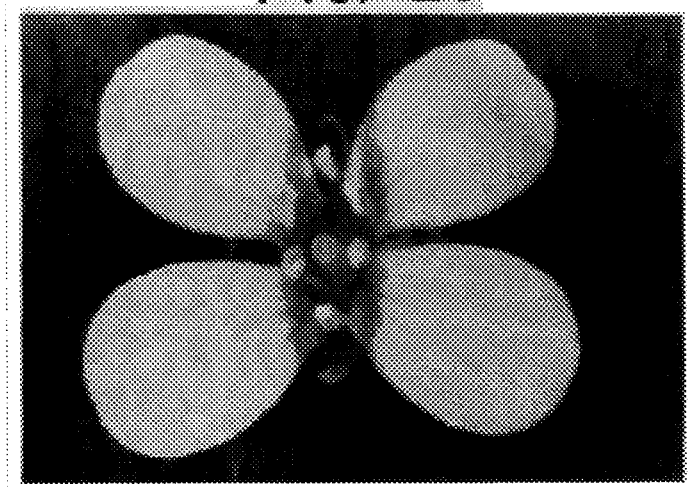
Figure 3A:
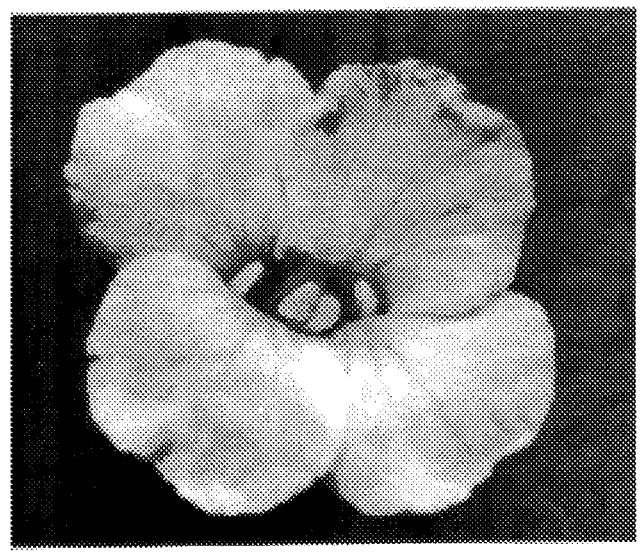
FIG. 3 shows a photograph of a flower (a) and flower organ (b) of rapeseed CMS lines SW18-3.
Figure 3B:
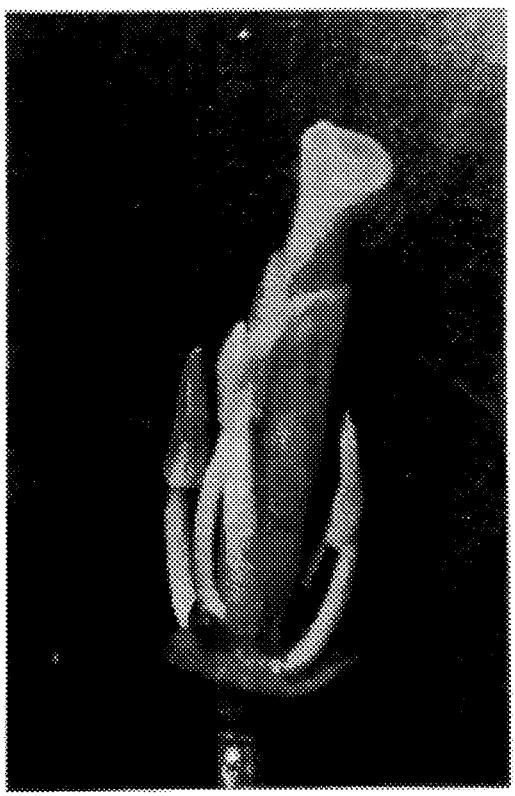

The structure of the flower of pollen recipient line SW18-3 is shown as photographs in FIGS. 2 and 3, which indicates that there is no development of pollen.

(2) Breeding of pollen-donor line

A hybrid plant was produced through hybridization of pollen-acceptor line SW18-3 and Chinese radish Yuanhong, incubation of ovary and incubation of embryo. Among the resultant hybrid plants, those which restored pollen fertility were selected as plants to which the Rf genes were introduced, and then subjected to backcross with Westar. Among the backcross first generation plants obtained, those which restored pollen fertility were selected, and then subjected to backcross in a similar manner further 6 times in total. In order to obtain homozygous Rf gene, the fertile plants were self-pollinated to obtain pollen-donor line ESW-7R. Alternatively, a donor line which has homozygous Rf gene was produced by pollen culture to obtain haploid plant and converting the haploid plant into diploid plant spontaneously or through the treatment with colchicine. The structure of the flower and the pollen fertility rate of the pollen-donor line ESW-7R were similar to those of normal rapeseed breed (Westar) whose pollen fertility rate is 95 to 98%. Since the cytoplasm of the pollen-donor line ESW-7R is originated from a male sterility cytoplasm of the pollen recipient line SW18-3, the Rf gene possessed by the pollen-donor line ESW-7R has a ability to restore completely the CMS derived from Kosena-radish.

(3) Breeding of $F_1$ hybrid plant

The pollen recipient line SW18-3 and the pollen-donor line ESW-7R were grown at 15° to 25° C. in an isolated greenhouse for seed collection which was protected from invasion by foreign pollens, and the F1 hybrid seed 0012-HY was obtained. The resultant $F_1$ hybrid seed was sowed, grown and examined for the appearance of male sterility strains during the flowering period. As a result, no sterile strains were detected. On the other hand, in case of commercially available $F_1$ hybrid Hyola 40 produced by utilizing Polima-derived CMS, about 30% strains were sterile (Table 3).

TABLE 3

| Condition for growing | Number of test strains | Number of sterile strains | Incidence of sterile strains (%) |
|---|---|---|---|
| 0012-HY | 52 | 0 | 0 |
| Hyola 40 | 37 | 11 | 29.7 |

Then, a seed obtained by mating the $F_1$ hybrid rapeseed 0012-HY with Westar was sowed and grown, and examined for the appearance of pollen fertility strains at the flowering period. As a result, the ratio of pollen fertility strains : sterile strains was about 1:3. It was confirmed that the restoration of fertility can be attributed to that the $F_1$ hybrid rapeseed 0012-HY has heterozygous Rf gene.

From the results described above, it can be anticipated that the pollen recipient line utilizing Polima-derived CMS caused restoration of fertility at relatively high incidence, resulting in the reduction in uniformity of $F_1$ hybrids. On the contrary, pollen recipient line utilizing Kosena-radish-derived CMS is considered to be useful to improve the uniformity of $F_1$ hybrids since there is no restoration of pollen fertility as is evident from Table 2 above.

We claim:

1. A method for introducing a fertility restorer gene of a Raphanus plant into a Brassica plant, which comprises:
   providing a Brassica plant having cytoplasm containing a cytoplasmic male sterility gene of a Raphanus plant which causes sterility of the Brassica plant,
   providing a Raphanus plant having a fertility restorer gene which can restore fertility to a plant containing the cytoplasmic male sterility gene, and
   conducting cell fusion or intergeneric cross directly between the Raphanus plant and the Brassica plant to introduce the fertility restorer gene of the Raphanus plant into the Brassica plant, to thereby produce a hybrid plant which has fertility restored by the fertility restorer gene.

2. The method according to claim 1, wherein the cytoplasmic male sterility gene is obtained from a radish selected from the group consisting of Raphanus sativus cv. Kosena, Raphanus sativus cv. Yuanhong and Raphanus sativus cv. Xinlimei.

3. The method according to claim 1, wherein the cell fusion is conducted by allowing a protoplast of the Brassica plant to fuse with a protoplast of the Raphanus plant having the fertility restorer gene, incubating the resultant fused cells to form colonies, and regenerating a whole plant from the colonies.

4. The method according to claim 3, wherein the fusion is an asymmetric fusion.

5. The method according to claim 4, wherein the asymmetric fusion is carried out using a protoplast of the Brassica plant treated with an iodinated compound and a protoplast of the Raphanus plant treated by irradiation.

6. The method according to claim 1, wherein the intergeneric cross is conducted between the Brassica plant and the Raphanus plant having the fertility restorer gene to obtain an embryo, and the embryo is then incubated.

7. The method according to claim 6, wherein the incubation of the embryo is followed by serial backcross.

8. The method according to any one of claims 1–7, wherein the Brassica plant is rapeseed plant Brassica napus.

9. The method according to any one of claims 1–7, wherein the Raphanus plant is radish plant Raphanus sativus.

10. The method according to claim 3, wherein the fused cells are incubated in a liquid medium.

11. The method according to claim 6, wherein the embryo is incubated in a solid medium.

12. A hybrid plant produced by the method of any one of claims 1–7 and 10–11.

13. A method for producing an $F_1$ hybrid of a rapeseed plant, which comprises:

hybridizing as a pollen recipient line a male sterile rapeseed plant CMS line to which CMS of Kosena-radish has been introduced and as a pollen donor line a rapeseed plant fertility restorer line to which a radish-derived fertility restorer gene capable of restoring pollen fertility against Kosena-radish-derived CMS has been introduced, to obtain the $F_1$ hybrid plant.

14. The method according to claim 13, wherein the radish-derived fertility restorer gene is introduced into the rapeseed plant fertility restorer line by means of cell fusion or intergeneric cross.

15. The method according to claim 14, wherein the cell fusion is conducted by allowing a protoplast of the rapeseed plant to fuse with a protoplast of the radish plant having the fertility restorer gene, incubating the resultant fused cells to form colonies, and regenerating a whole plant from the colonies.

16. The method according to claim 15, wherein the fusion is an asymmetric fusion.

17. The method according to claim 16, wherein the asymmetric fusion is carried out using a protoplast of the rapeseed plant treated with an iodinated compound and a protoplast of the radish plant treated by irradiation.

18. The method according to claim 14, wherein the intergeneric cross is conducted between the rapeseed plant and the radish plant having the fertility restorer gene to obtain an embryo, and the embryo is then incubated.

19. The method according to claim 18, wherein the incubation of the embryo is followed by serial backcross.

20. An $F_1$ hybrid of a rapeseed plant produced by the method according to any one of claims 13 to 19 wherein the pollen fertility of the male sterile plant resulting from Kosena radish-derived CMS has been restored in the $F_1$ hybrid plant.

* * * * *